United States Patent
Schick et al.

[11] Patent Number: 6,134,298
[45] Date of Patent: Oct. 17, 2000

[54] FILMLESS DENTAL RADIOGRAPHY SYSTEM USING UNIVERSAL SERIAL BUS PORT

[75] Inventors: David B. Schick, Flushing; Valeriy Armencha, White Plains, both of N.Y.

[73] Assignee: Schick Technologies, Inc., Long Island City, N.Y.

[21] Appl. No.: 09/131,061

[22] Filed: Aug. 7, 1998

[51] Int. Cl.$^7$ ........................................... H05G 1/64
[52] U.S. Cl. ........................... 378/98.8; 250/370.09
[58] Field of Search ................... 378/98.8, 191; 250/370.09

[56] References Cited

U.S. PATENT DOCUMENTS

| | | |
|---|---|---|
| 4,611,347 | 9/1986 | Netravali et al. . |
| 5,434,418 | 7/1995 | Schick . |
| 5,568,192 | 10/1996 | Hannah . |
| 5,610,657 | 3/1997 | Zhang . |
| 5,712,682 | 1/1998 | Hannah . |
| 5,742,407 | 4/1998 | Albrecht et al. . |
| 5,773,832 | 6/1998 | Sayed et al. ........................ 378/98.8 |
| 5,777,254 | 7/1998 | Fay et al. . |
| 5,778,218 | 7/1998 | Gulick . |
| 5,912,942 | 6/1999 | Schick et al. ........................ 378/98.8 |

FOREIGN PATENT DOCUMENTS

| | | |
|---|---|---|
| 0583908A | 2/1994 | European Pat. Off. . |
| WO9603917A | 2/1996 | WIPO . |
| WO9810587A | 3/1998 | WIPO . |
| WO9815227A | 4/1998 | WIPO . |
| WO9820796A | 5/1998 | WIPO . |

OTHER PUBLICATIONS

Product Brochure for Connectix Quickcam, Connectix Corp., 2655 Campus Drive, San Mateo, CA 94403.
User's Guide for Kodak ds DVC 300 Digital Video Camera.

*Primary Examiner*—Craig E. Church
*Attorney, Agent, or Firm*—Fitzpatrick, Cella, Harper & Scinto

[57] ABSTRACT

A filmless dental radiography system includes an intraoral sensor that outputs image data and a computer having a universal serial bus port that receives data. The image data output by the intraoral sensor are input to the computer through the universal serial bus port.

16 Claims, 2 Drawing Sheets

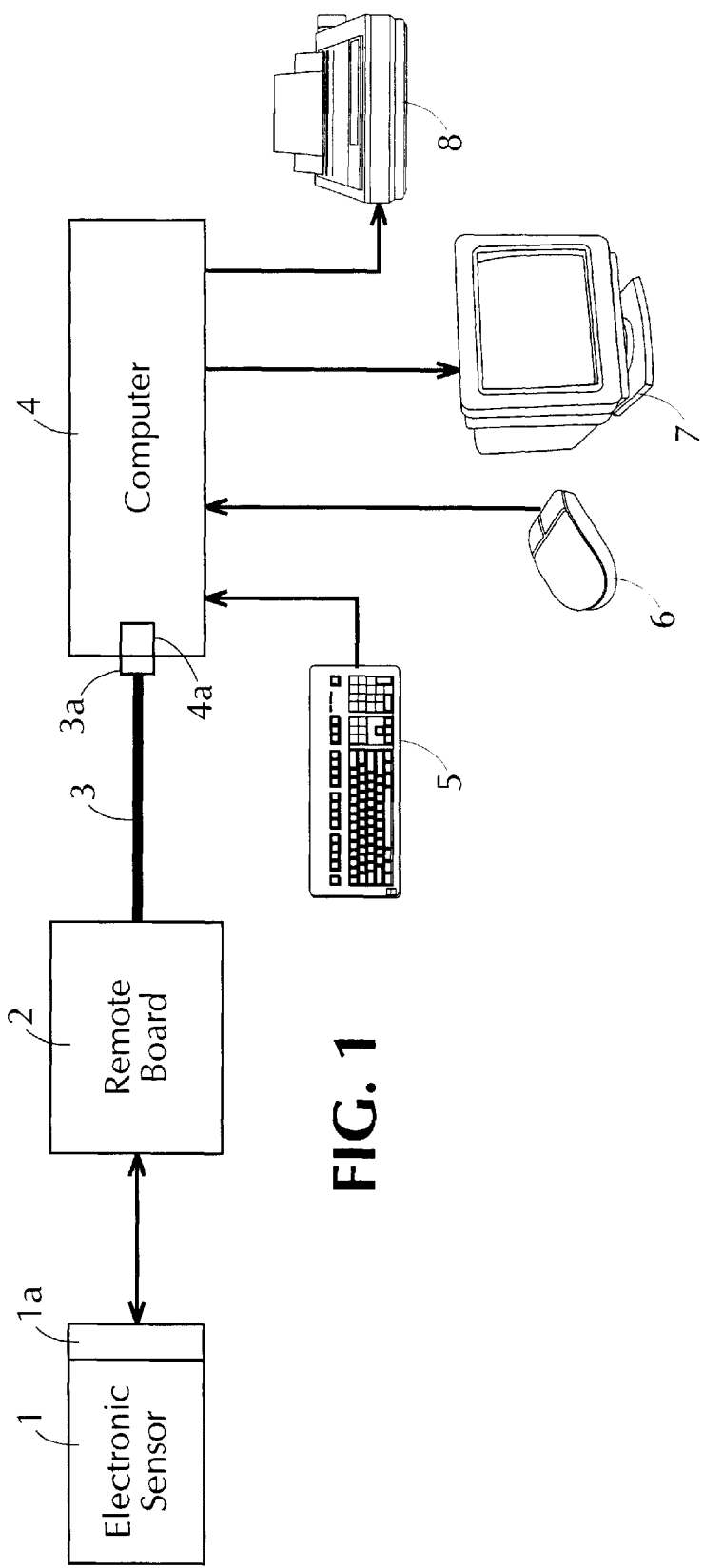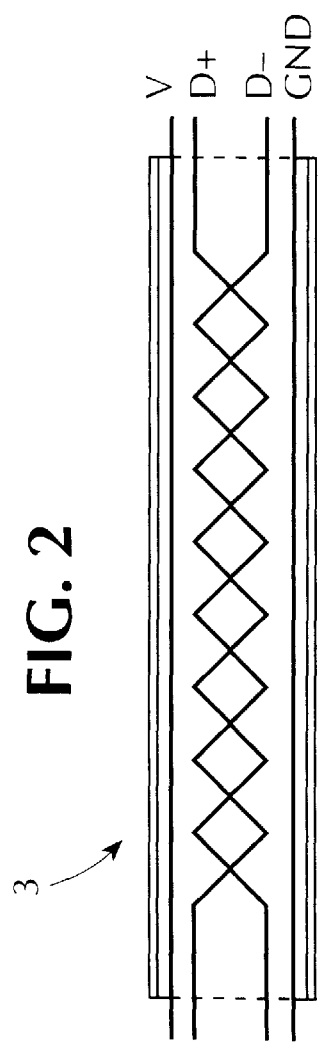

FILMLESS DENTAL RADIOGRAPHY SYSTEM USING UNIVERSAL SERIAL BUS PORT

BACKGROUND OF THE INVENTION

1. Field of the Invention

This invention relates to a filmless dental radiography system, and more particularly to a filmless dental radiography system that includes an intraoral radiation sensor that interfaces with the Universal Serial Bus (USB) port of a desktop, tower or portable (such as laptop or notebook) computer.

2. Description of the Related Art

Dentists and oral surgeons typically use x-radiation ("x-rays") to obtain images of their patients' teeth, mouths and gums to aid in diagnosis and treatment. In traditional oral and dental radiography, a cartridge containing a piece of photographic film is placed in the patient's mouth, for example behind a patient's tooth, and an x-ray beam is projected through the tooth and onto the film. The film, after being exposed in this manner, is developed in a dark room or a closed processor using special chemicals to obtain a photographic image of the tooth.

More recently, the field of filmless dental radiography has emerged. In filmless dental radiography, an x-ray beam is still projected through the patient's tooth, but no photographic film is used. Instead, an electronic sensor is placed in the patient's mouth behind the tooth to be examined. The electronic sensor may include a charge-coupled device (CCD), an active pixel sensor (APS) array or any other filmless radiation sensor. The x-rays pass through the tooth and impinge on the electronic sensor, which converts the x-rays into an electrical signal. The electrical signal is transmitted over a wire to a computer, either directly or though a module containing intermediate processing circuitry. The computer then processes the signal to produce an image on an associated output device, such as a monitor or a printer.

Filmless dental radiography offers several advantages over traditional film-based radiography. Most importantly, the electronic sensor is much more sensitive to x-rays than is film, allowing the dosage of x-rays to the patient to be lowered by as much as 90%. Also, the image of the tooth is generated by the computer almost instantaneously, thus eliminating the entire developing process, including the use of potentially harmful chemicals. In addition, because the images are generated electronically, they can be stored electronically in a computer database.

Examples of filmless dental radiography systems include those described in U.S. Pat. No. 4,160,997 to Robert Schwartz and U.S. Pat. No. 5,434,418 to David Schick. Filmless dental radiography systems typically utilize a standard desktop computer, such as an IBM or IBM compatible type personal computer. To provide a data path between the electronic sensor (or the intermediate module) and the computer's CPU, some conventional systems use the computer's Peripheral Component Interconnect (PCI) bus. The PCI bus, a internal 32-bit local bus that runs at 33 MHz and carries data at up to 133 megabytes per second (MBps). Other conventional filmless dental radiography systems use the computer's Industry Standard Architecture (ISA) bus, an 8- or 16-bit internal bus that carries data at up to 8.33 MBps. Each of these buses may act as a suitable interface between the sensor and computer.

While generally good for their intended applications, systems that use the computer's PCI or ISA bus have certain drawbacks. Most notably, the PCI and ISA buses are internal, and require that a specially designed circuit board be installed inside of the computer. The need for such a board increases the cost and reduces the reliability of the overall system.

Moreover, installing such a board is a time-consuming task that may only be performed by someone trained in the installation of computer peripherals. In particular, the installation requires the physical opening of the computer's housing, the clearing of any casing or wiring that may be in the way of the slot, the insertion of the card into the slot and the re-assembly of the housing once the insertion is complete. These are not tasks that are easily performed by the typical user of a filmless dental radiography system, such as a dentist, endodontist or oral surgeon.

In addition, many practitioners use a single sensor in conjunction with several computers, such as having a separate computer associated with each patient chair in the practitioners office. For such a scenario to be practical, a separate board must be installed into each of the computers, further increasing the cost of the overall system.

Moreover, the number of PCI and ISA slots available in a desktop or tower computer is limited. Installing a circuit board in a given slot to support a filmless dental radiography system precludes the use of that slot for some other type of peripheral device. Once all slots for a given bus are used, no more peripherals can be interfaced through that bus, unless one of the installed boards is removed and replaced with the board for the new peripheral. Such removal and replacement is not something that can be conveniently done on a regular basis.

Further still, portable computers, such as laptops and notebooks, generally are not provided with PCI or ISA slots. Accordingly, a conventional filmless dental radiography system cannot be used with such portable computers.

Very recently, desktop, tower and portable computers are being made available with a Universal Serial Bus (USB) port. The USB is a serial 12 megabit per second (Mbps) channel that can be used for peripherals. The USB is a token-based bus. In particular, the USB host controller broadcasts tokens on the bus and a device that detects a match on the address in the token responds by either accepting or sending data to the host. The host also manages USB bus power by supporting suspend/resume operations.

Unlike the PCI and ISA buses, the USB port does not require the use of a specially designed circuit board inside the computer. Accordingly, once the appropriate software has been installed, a peripheral simply need be plugged into the USB port to be ready for operation. In addition, one device can be unplugged and another plugged in without changing the hardware configuration of the computer.

Also, the USB port is "hot swappable," meaning that a first peripheral may be unplugged and a second peripheral plugged in without turning off and restarting the computer. In addition, the USB uses tiered star topology, allowing up to 127 different peripherals on the bus at a time. Further still, not only desktop and tower computers have USB ports; laptop and notebook computers are provided with USB ports as well.

While the USB port has received a great deal of attention from those designing computer peripherals as of late, no one has heretofore thought to use it as an interface for a filmless dental radiograph system. This is primarily because the USB is much slower than the PCI or ISA buses. More particularly, the theoretical maximum bandwidth of the USB is 12 Mbps (1.5 MBps), several times slower than the 8.33 MBps ISA bus and orders of magnitude slower than the 133 MBps PCI bus. And because many peripherals might be connected to the USB, no single peripheral can expect to realize the full range of the 1.5 MBps maximum theoretical bandwidth of the USB, making the practical bandwidth of the USB substantially less.

Accordingly, the USB is not believed to be fast enough to support the data flow requirements of a scientific sensor, such as a filmless dental radiography sensor. For example, in a conventional filmless dental radiography system analog data might be read-out of the sensor at a rate on the order of 4 million pixels per second (Mpps), converted on a real-time basis to digital data by an analog-to-digital converter (ADC) in an intermediate module and provided on a real-time basis to the computer's PCI or ISA bus. If a 16-bit (2 byte) ADC is used, an interface that can carry data at 8 MBps is required for such data transfer. This is several times greater than even the 1.5 MBps theoretical maximum bandwidth of the USB. Even a system which reads-out data at rate of 1 Mpps and uses a 12-bit (1.5 byte) ADC requires 1.5 MBps of bandwidth, the theoretical maximum bandwidth of the USB, and would strain or exceed the capabilities of the USB.

Some computer peripherals, such as digital cameras, have relatively low image quality requirements, and contend with the relatively smaller of the USB by simply reading-out data more slowly. This approach, however, is not suitable for a scientific sensor such a filmless dental radiography system, in which the quality of the image is paramount. In particular, a slower read-out rate results in a greater accumulation of dark signal (i.e. that part of the image data created by thermally generated electron-hole pairs) in the sensor, which results in turn in greater image degradation. Such results, while perhaps acceptable for a digital camera, are completely unacceptable for a scientific sensor such as a filmless dental radiography system, which must produce images of clarity sufficient to facilitate the diagnosis and treatment cavities, dental roots and the like.

There is a need, therefore, for a filmless dental radiography system that solves the inherent problems associated with the PCI and ISA buses by exploiting the advantages of using the USB port, while at the same time overcoming the obstacles that have heretofore prevented the USB port from being used for scientific sensors.

SUMMARY OF THE INVENTION

One object of the present invention is to provide a filmless dental radiography sensor that does not exhibit the disadvantages of using the PCI or ISA buses that are discussed above.

Another object of the present invention is to provide a filmless dental radiography system that uses the computer's USB port as the interface between the sensor and the computer.

In accordance with one aspect of the present invention, a filmless dental radiography system is provided which includes an intraoral sensor that outputs image data and a computer having a universal serial bus port that receives data. The image data output by said intraoral sensor are input to the computer through the universal serial bus port.

In accordance with another aspect of the present invention, a filmless dental radiography system is provided which includes an intraoral sensor that outputs image data, a computer having a universal serial bus port that receives data and a universal serial bus cable between the intraoral sensor and the computer with the universal serial bus cable including a universal serial bus plug that couples with the universal serial bus port. The image data output by the intraoral sensor are input to the computer over the cable and through the universal serial bus port.

In accordance with another aspect of the present invention, an intermediate circuit is interposed between the sensor and the computer which includes a processing circuit that controls the reading-out of image data from the intraoral oral sensor and a memory circuit in which the image data read-out of the intraoral sensor are stored.

In accordance with yet another aspect of the present invention, the processing circuit retrieves the image data stored in the memory, processes the image data and output the image data to the computer through the universal serial bus port, at a rate slower than the rate at which the image data were read-out from the intraoral sensor.

In accordance with yet another aspect of the present invention, the processing circuit is a specially programmed reduced instruction set computer.

In accordance with yet another aspect of the present invention, the intraoral sensor includes a charge coupled device.

In accordance with yet another aspect of the present invention, the intraoral sensor includes an active pixel sensor array.

BRIEF DESCRIPTION OF THE DRAWINGS

FIG. 1 is a block level illustration of one embodiment of the filmless dental radiography system of the present invention.

FIG. 2 is a cross-sectional illustration of the USB cable used in the filmless dental radiography system of the present invention.

DETAILED DESCRIPTION OF THE PREFERRED EMBODIMENTS

Figure 3:
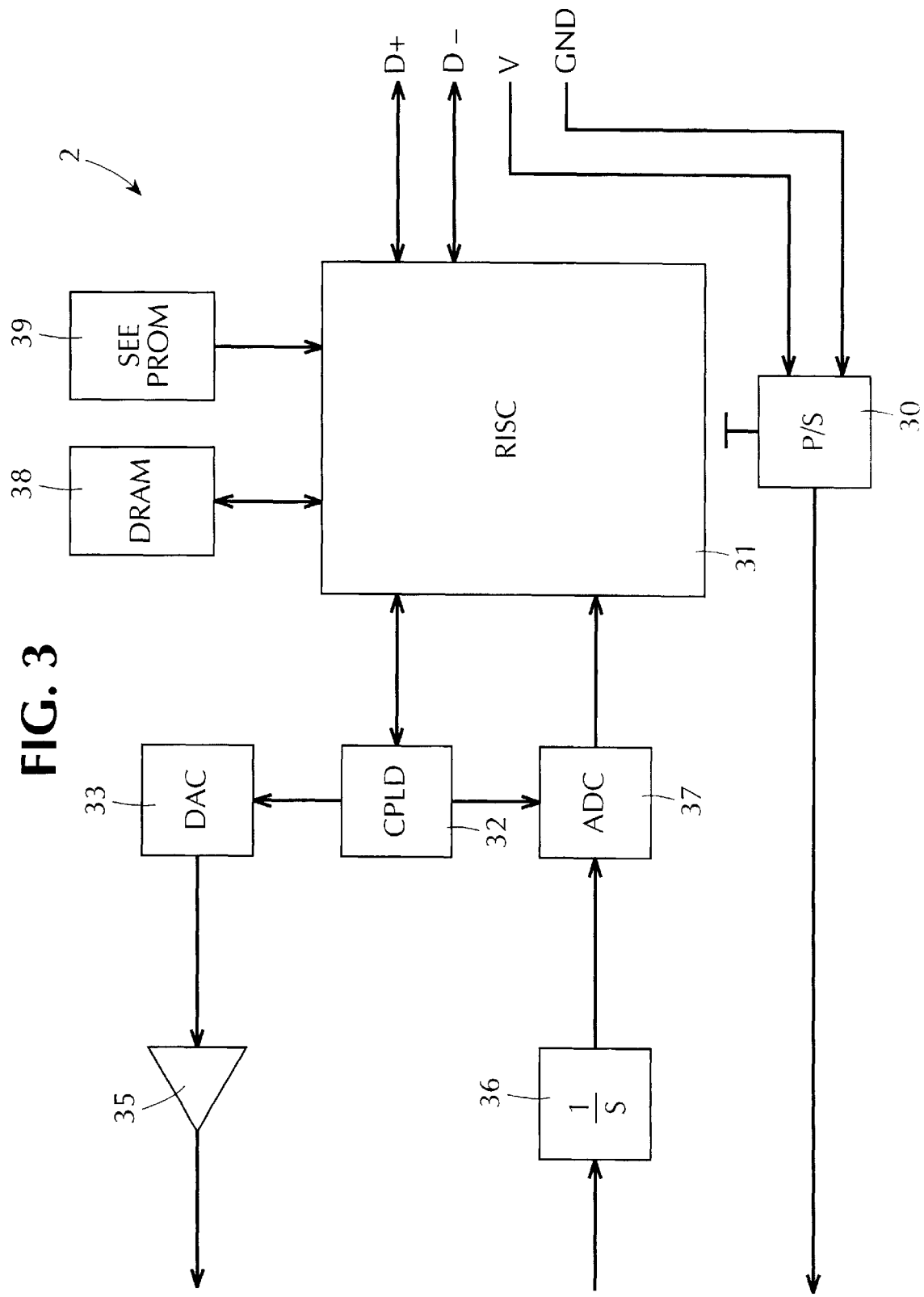
FIG. 3 is a functional block diagram of one embodiment of the remote board of the present invention.

An embodiment of a filmless dental radiography system according to the present invention is depicted in FIG. 1. As can be seen, the system includes an electronic sensor 1, including a connector 1a, a remote board 2 and a computer 4, with the remote board 2 and the computer 4 being connected through the computer's USB port 4a. The electronic sensor 1 may comprise a CCD, an APS array or some other solid state device capable of converting electromagnetic radiation into electrical signals. The electronic sensor 1 might also comprise on top of the CCD, APS array or other solid state device a scintillator layer which converts x-rays into visible light.

The computer 4 may be any conventional desktop, tower, laptop or notebook computer that is equipped with a USB port 4a and a corresponding USB channel. In addition to the USB port 4a, the computer 4 is equipped with various known software modules that support the USB channel, such as USB host controller software, and a known USB hardware interface.

The computer 4 is either connected to or has built in one or more input devices, such as a keyboard 5 and a mouse 6, and one or more output devices, such as a monitor 7 and a printer 8. These devices allow the user to control the operation of the system, and to view the dental images that the system creates. The computer might also include or be connected to some type of storage device (not shown), such as a hard drive, for permanent storage of the images in patient files.

Image data flows from the electronic sensor 1 to the USB port 4a through the remote board 2. The remote board 2 and USB port 4a are physically connected through a standard USB cable 3 which includes a USB plug 3a that couples with the USB port 4a. The USB cable 3, illustrated schematically in FIG. 2, is a four-wire bi-directional cable that includes a power line V, a data plus line D+, a data minus line D− and a ground line GND. This cable carries serial image data from the remote board 2 to the USB port 3a, and also carries serial control instructions from the USB port 3a to the remote board 2, such as for example tokens broadcasted by the USB host controller software.

One preferred embodiment of the remote board 2 present invention is depicted in FIG. 3. In this preferred embodiment, the remote board 2 includes all of the processing circuitry necessary to, among other things, effect x-ray signal integration by the electronic sensor 1; read-out analog data from the electronic sensor 1 at the high rate required for a scientific sensor; convert the analog data to digital data; store that digital data; process that data into a form suitable for transmission over the USB channel; and transmit the processed data to the computer 4 via the USB port 4a at a rate slow enough for the USB channel to support. The remote board 2 also includes a power supply module that couples with the V and GND lines of the USB to receive power and provide the appropriate voltages to the electronic sensor 1 and the other components on the remote board 2.

The core of the remote board 2 in this preferred embodiment is a reduced instruction set computer (RISC) chip 31. An example of an appropriate RISC chip is the SL11-R-USB Controller (manufactured by ScanLogic Corporation, 4 Preston Court, Bedford, Mass. 01730, http//:www.scanlogic.com), a 48 Mhz, 16-bit RISC with a built-in 3K×16 BIOS Mask ROM, a 1.5 K×16 internal SRAM, a 2 Mbyte SRAM/DRAM memory interface port, a 12 Mbps (1.5 MBps) USB port, an 8- or 16-bit direct memory access (DMA) or input/output (I/O) port, a serial EEPROM (SEEPROM) interface and four high-speed pulse width modulation or programmable output channels. The full description of the SL11-R-USB RISC can be found in the "SL11R/SL16/SL11P2USB/SL08/SLEPP2USB Hardware Specification," published by ScanLogic Corporation. Under the control of firmware specific to the type of electronic sensor that the system incorporates, the RISC chip 31 receives signals from and interfaces with the USB host controller software, and produces signals that control all aspects of the electronic sensor's operation, including data read-out and x-ray signal integration.

The remote board 2 includes two memory blocks—a random access memory DRAM 38 for storing the image data read-out of the sensor and a read-only memory SEEPROM 39 for storing system initialization programs, test programs, USB support programs and configuration data. DRAM 38 may be accessed by the RISC chip 31 either via software or via DMA.

A complex programmable logic device (CPLD) 32 decodes signals from RISC chip 31 to provide specific control signals to electronic sensor 1 and to other components on the remote board 2. More particularly, CPLD 32 generates digital signals that are provided to a digital-to-analog converter (DAC) 34, which DAC 34 in turn converts those digital signals into analog voltages suitable for effecting x-ray signal integration by and read-out of electronic sensor 1. These analog voltages are provided to electronic sensor 1 via a buffer 35.

The analog data read-out of electronic sensor 1 are provided to an input filter 36 (which may be, for example, a fourth-order Bessell low-pass filter), and from there to analog-to-digital converter (ADC) 37. ADC 37, under the control of CPLD 32, converts the analog data retrieved from electronic sensor 1 into digital data that can be processed by RISC chip 31.

To ensure that the data corresponding to a captured image is retrieved before a unacceptable amount of dark signal can accumulate, the reading-out of the sensor is performed at a relatively high rate, such as for example rates on the order of 1 Mpps or more. These read-out rates, in conjunction with an ADC of 16-, 12- or even 8-bits, however, result in data transfer rates that are either close to or exceed the theoretical 1.5 MBps maximum bandwidth of the USB, and are therefore too fast for the USB to support. Accordingly, the data retrieved from electronic sensor 1 are stored temporarily in DRAM 38. After being stored in DRAM 38, the data are read-out by RISC chip 31 and assembled into a USB-compatible format. The RISC chip 31 might also be programmed to perform other required or desirable processing operations as well, such as for example dark signal subtraction.

The assembled and processed data are then transmitted under the control of RISC chip 31 to the USB port 4a of the computer 4. Due to the bandwidth constraints of the USB, this transmission occurs at a rate slower than the rate at which the image data were read-out of electronic sensor 1, and which the USB can comfortably support. For example, if the filmless dental radiography system is the only peripheral connected to the USB port 4a, the transfer will take place at rates on the order of 750 kilobytes per second (KBps). If on the other hand several peripherals are connected to the USB port 4a, such as via a hub, the data transfer will take place at rates slower than that. In any event, the rate of transfer of the data over to the USB port 4a will have no effect on the quality of the image, since the data is being not being read-out of the sensor at the slower rate, but rather out of the DRAM 38.

The unique approach of the present invention allows data to be read-out of the electronic sensor 1 at a fast rate to prevent the accumulation of an unacceptably high amount of dark signal, while at the same time exploiting the advantages of the computer's USB without exceeding or straining its bandwidth limitations.

It is to be understood that the above description and drawings are illustrative of the present invention and detail contained therein are not to be construed as limitations thereon. Changes in components, procedure and structure may be made without departing from the scope of the present invention as defined in the following claims.

What we claim is:

1. A filmless dental radiography system comprising:
   an intraoral sensor that outputs dental image data;
   an intermediate circuit that reads-out the dental image data from said intraoral sensor at a first rate and outputs the dental image data at a second rate slower than the first rate; and
   a computer having a universal serial bus port that receives data,
   wherein the dental image data output by said intermediate circuit are input to said computer through the universal serial bus port.

2. A filmless dental radiography system according claim 1, wherein said intermediate circuit includes a processing circuit that controls the reading-out of dental image data from said intraoral oral sensor.

3. A filmless dental radiography sensor according to claim 2, wherein said intermediate circuit further includes a memory circuit.

4. A filmless dental radiography sensor according to claim 3, wherein the processing circuit stores the dental image data read-out from said intraoral sensor in the memory circuit.

5. A filmless dental radiography system according to claim 4, wherein the processing circuit is specially programmed reduced instruction set computer.

6. A filmless dental radiography system according to claim 5, wherein said intraoral sensor comprises a charge coupled device.

7. A filmless dental radiography system according to claim 5, wherein said intraoral sensor comprises an active pixel sensor array.

8. A filmless dental radiography system comprising:

an intraoral sensor that outputs dental image data;

an intermediate circuit that reads-out the dental image data from said sensor at a first rate and outputs the dental image data at a second rate slower than the first rate;

a computer having a universal serial bus port that receives data; and a universal serial bus cable between said intermediate circuit and said computer, said universal serial bus cable including a universal serial bus plug that couples with the universal serial bus port of said computer, wherein the dental image data output by said intermediate circuit are input to said computer over said universal serial bus cable and through the universal serial bus port.

9. A filmless dental radiography system according to claim 8, wherein said intermediate circuit includes a processing circuit that controls the reading-out of dental image data from said intraoral oral sensor.

10. A filmless dental radiography system according to claim 9, wherein said intermediate circuit further includes a memory circuit.

11. A filmless dental radiography system according to claim 10, wherein the processing circuit stores the dental image data read-out of said intraoral sensor in the memory circuit.

12. A filmless dental radiography system according to claim 11, wherein the processing circuit is a specially programmed reduced instruction set computer.

13. A filmless dental radiography system according to claim 12, wherein said intraoral sensor comprises a charge coupled device.

14. A filmless dental radiography system according to claim 12, wherein said intraoral sensor comprises an active pixel sensor array.

15. A filmless dental radiography system comprising:

intraoral means for converting an x-ray signal representing a dental image into electrical dental image data;

means for reading-out the electrical dental image data from said intraoral means at a first rate and outputting the electrical dental image data at a second rate slower than the first rate; and processing means for processing said electrical dental image data to produce a image suitable for display, wherein said processing means includes a universal serial bus port that receives the electrical dental image data at the second rate.

16. A method of providing a dental image, comprising the steps of:

converting an x-ray signal representing a dental image into electrical dental image data;

reading-out the electrical dental image data at a first rate; and providing the electrical dental image data to the universal serial bus port of a computer at a second rate slower than the first rate.

* * * * *